United States Patent [19]

Mikhail

[11] Patent Number: 5,342,364

[45] Date of Patent: Aug. 30, 1994

[54] PATELLAR IMPLANT STEM TRIMMER

[76] Inventor: W. E. Michael Mikhail, 4203 Shamley Green, Toledo, Ohio 43623

[21] Appl. No.: 62,793

[22] Filed: May 17, 1993

[51] Int. Cl.$^5$ ............................................. A61B 17/36
[52] U.S. Cl. ...................................... 606/79; 606/86; 606/88
[58] Field of Search ..................... 606/79, 86, 87, 88

[56] References Cited

U.S. PATENT DOCUMENTS

| | | | |
|---|---|---|---|
| 4,633,862 | 1/1987 | Petersen | 606/88 |
| 5,108,401 | 4/1992 | Insall et al. | 606/79 |
| 5,129,908 | 7/1992 | Petersen | 606/86 |
| 5,250,050 | 10/1993 | Poggie et al. | 606/79 |

Primary Examiner—Stephen C. Pellegrino
Assistant Examiner—Sonya C. Harris
Attorney, Agent, or Firm—Emch, Schaffer, Schaub & Porcello

[57] ABSTRACT

A tool intended to facilitate the trimming of the stem of a patellar prosthesis to adapt the length of the stem to fit differing cross-sectional thickness of a human patella is disclosed. The trimming tool includes a seat area for receiving the prosthesis and a cap member for securing the prothesis in the seat. The cap area includes an aperture therethrough which exposes a specific length of stem for trimming. A cutting guide on the cap member ensures that the stem is cut in a perpendicular orientation to the centerline axis of the prosthesis.

16 Claims, 3 Drawing Sheets

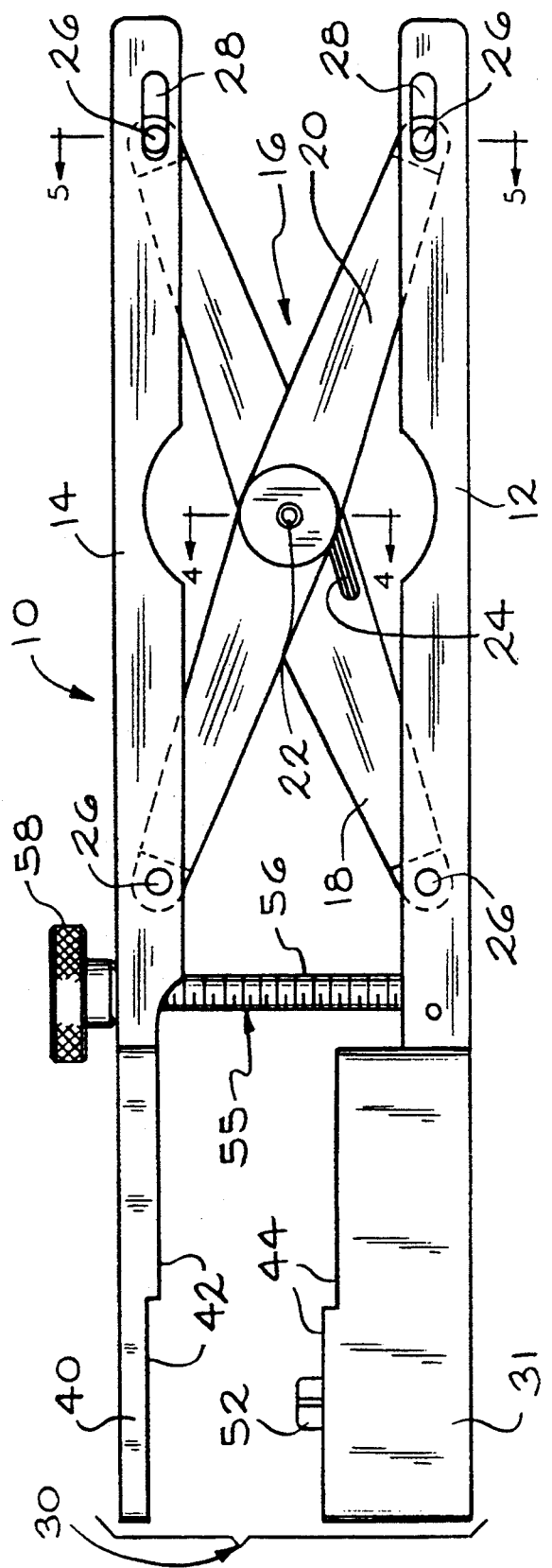
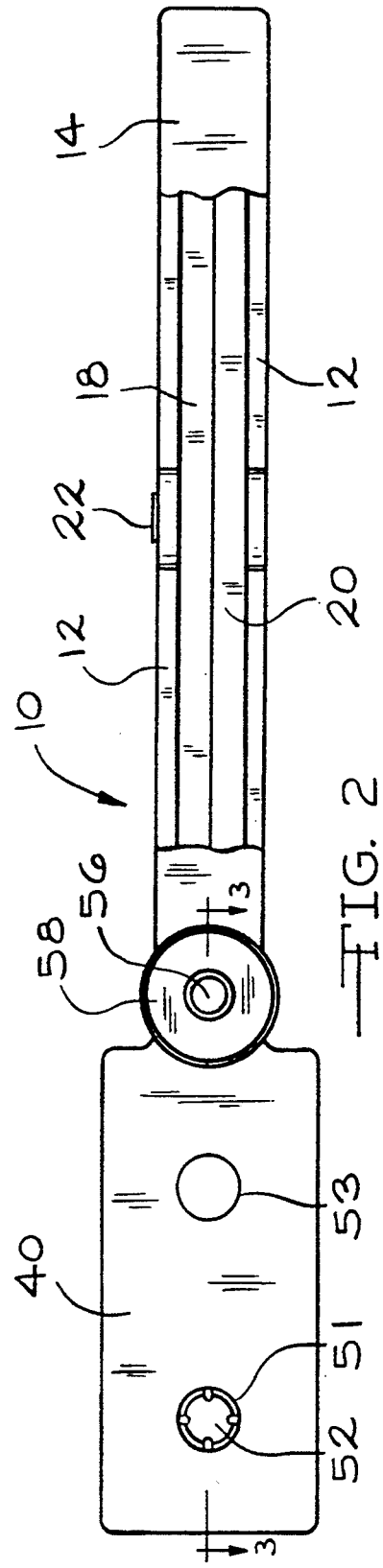

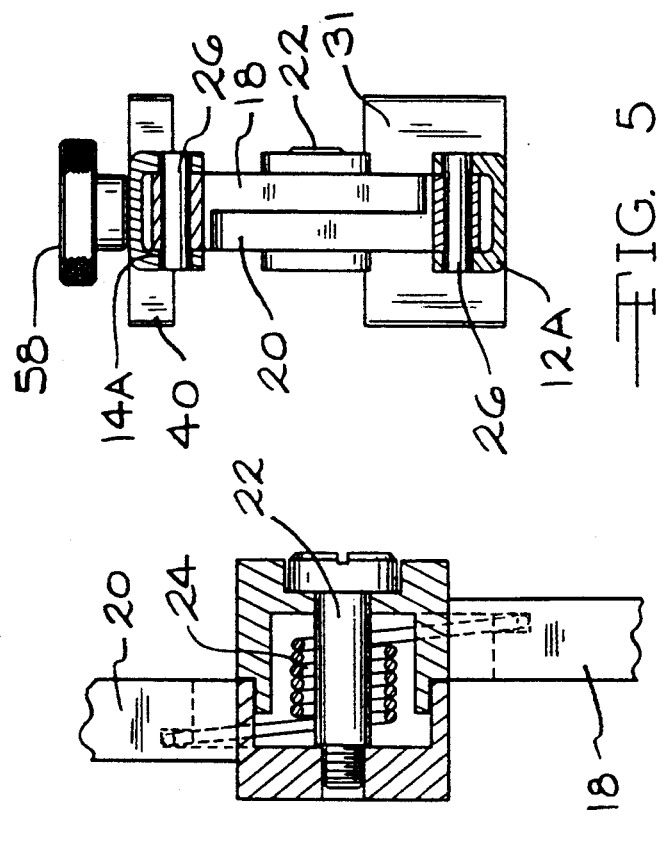
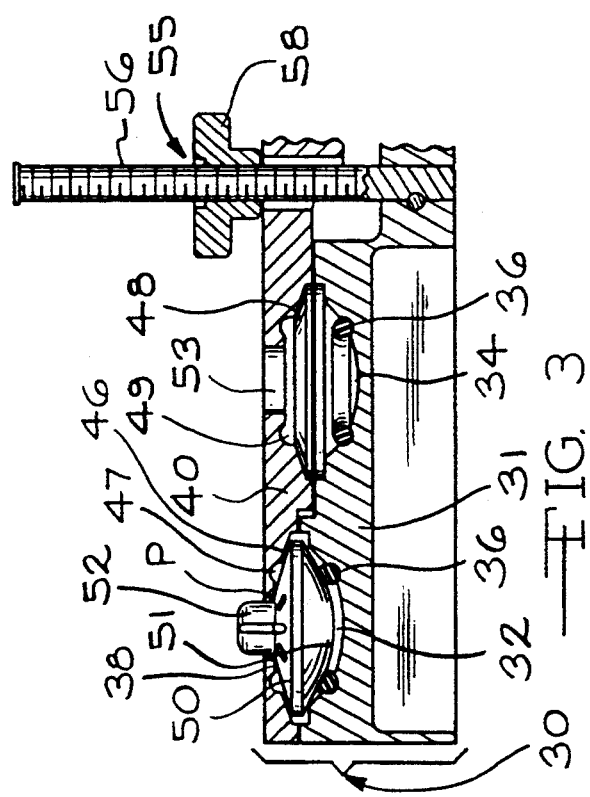

1

PATELLAR IMPLANT STEM TRIMMER

BACKGROUND ART

The present invention is directed to a stem trimmer for use with patellar prostheses which are implanted in a human patella during total knee replacement surgery. In such surgery, it is common to provide a prosthesis in which one component is fastened to the distal end of the femur which has been resected and another component is fastened to the proximal end of the tibia which has been resected so that the two components will act together in permitting the leg to bend and straighten. In performing such surgery, the patella is not normally replaced but rather resurfaced such that the interior crown portion facing the condyles is cut and reamed to form a cavity in which a patellar prosthesis is implanted. The patellar prosthesis has a crown facing inwardly to engage the patella or trochlear groove of the femoral component.

Patellar prostheses come in all shapes and sizes, however, the newest designs now commonly include a body portion having a tapered surface on the side away from the crown. One such prosthesis design is the subject matter of U.S. patent application Ser. No. 07/508,088, filed Oct. 18, 1990 by the Applicant herein. Most patellar prostheses are intended to meet a stated objective of providing a functional resurfacing of the patella while eliminating as much damage and disfigurement of the patella, resulting from the implant, as possible. Human patellas are notoriously fragile and are found in a variety of shapes and cross-sections Thus, patellar implants need to be customized and sized to the patient during the replacement surgery. It is therefore desirable to utilize a patellar implant which requires a minimal amount of cutting or removal of the patient's patella in order to securely fix the patellar implant within the patella.

There are a number of factors, not the least of which is patient size, which require that patellar implants be of a number of different sizes while generally incorporating the following features. The patellar implant will usually have a domed crown facing outwardly from the patella for engagement with the condylar or trochlear groove of a femoral prosthesis component and a body portion having a stem or central post extending outwardly from the body portion in opposition to the crown. The central post or stem is intended to be fixed within a recess cut into the patella, thus securing the implant in place. The size of the body portion and length of the stems of the patellar implants will vary according to patient patella size and cross-section. In keeping with meeting the objective of minimizing damage and disfigurement of the patella structure while providing for secure entrenchment of the implant within the patella, it is a standard procedure to customize the length of the stem to accommodate the patella cross-sectional thickness.

The stem of the patellar implant is fit within a cavity reamed from the patella during the surgical procedure. It is imperative that the post and cavity provide a snug fit to ensure that the implant remains securely fixed to the patella. Since the depth of the cavity is dependent upon the cross-sectional thickness of the patella, the post, is many times, modified or truncated to meet the particular demands of the subject patella. Particular attention is required during truncation of the stem to ensure that the end of the post is squared and perpendicularly oriented with the central axis of the implant. Problems have been encountered in the situation where there is angular deviation on the end of the post; the patellar implant many times will be prevented from proper orientation within the cavity provided in the patella.

It is an object of the present invention to provide a tool for assisting in truncating or trimming the stem or post of a patellar implant.

It is yet another object of the invention to provide a tool which is adaptable to trim or truncate the stem or post of a patellar implant to various desired lengths.

It is yet a further object of the invention to provide a tool adaptable to receive patellar prostheses or implants of various sizes to trim or truncate the stem of the implant.

Yet another object of the invention is to provide a tool adaptable to receive patellar prostheses of various sizes and to trim or truncate the stem or post of the implant to various desired lengths.

These objects and others which will become readily apparent are met by the patellar stem trimmer of the present invention.

DISCLOSURE OF INVENTION

The present invention provides a tool intended for use in trimming the post or stem of a patellar prosthesis to adapt the length of the stem of the prosthesis to fit differing cross-sectional thicknesses of a human patella. The tool of this invention can be used to trim a patellar prosthesis having a stem or central post of any design or configuration. In keeping with the objective of maintaining as much natural patellar structure as possible, the surgeon upon determining the thickness of the patella will use the present invention to trim the stem to an appropriate length which will serve to securely retain the implant in position within the patella while at the same time optimizing the removal of a minimal amount of patella material. The stem trimmer of this invention includes a prosthesis retention member having a seat area for holding the patellar prosthesis and a cap member for securely orienting the patellar prosthesis and allowing a specified portion of the stem of the prosthesis to be exposed to a cutting guide. The exposed portion of the stem is then trimmed away, leaving the distal trimmed surface of the stem oriented perpendicularly to the axis of the stem. The cap member is movable along the axis of the stem to engage and disengage with the seat member. The seat member and cap member are each fixed to first and second grip members, respectively. The grip members are interjoined by means of a scissor guide designed to keep the grip members in parallel relationship during movement of the cap member with respect to the seat member.

The invention will be more readily understood with reference to the following detailed description in conjunction with the attached drawings.

BRIEF DESCRIPTION OF THE DRAWINGS

FIG. 1 is a side elevational view showing the patellar stem trimmer of the present invention.

FIG. 2 is a top plan view of the patellar stem trimmer of FIG. 1.

FIG. 3 is a sectional view taken along line 3—3 of FIG. 2.

FIG. 4 is a sectional view taken along line 4—4 of FIG. 1.

FIG. 5 is a sectional view taken along line 5—5 of FIG. 1.

BEST MODE OF CARRYING OUT THE INVENTION

Figure 6:
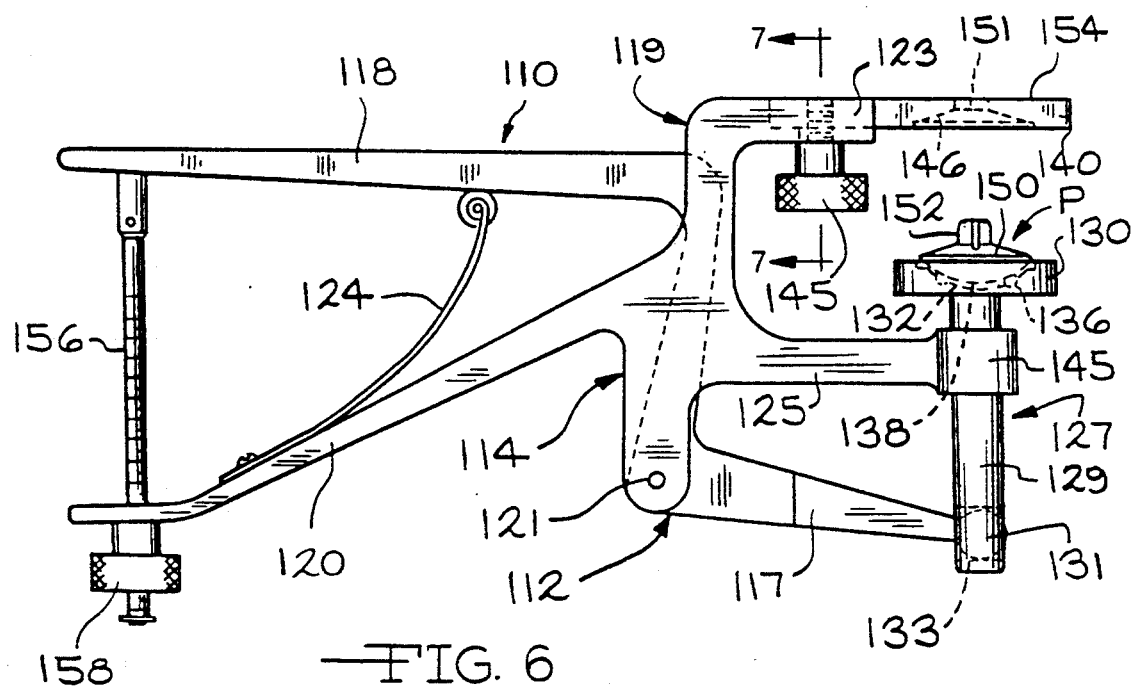
FIG. 6 is a side elevational view of an alternative embodiment of the patellar stem trimmer of the present invention.

Referring now to FIGS. 1-5, there is shown a patellar stem trimmer generally designated by numeral 10. The stem trimmer 10 is preferably constructed to have a first grip member 12 and a second grip member 14 which are interjoined together and maintained in parallel relationship by a scissor guide 16. The scissor guide 16 includes a first arm 18 which is engaged for rotation at one end with the first grip member 12 and engaged for sliding movement at its opposed end with the second grip member 14. The second arm 20 of the scissor guide 16 is engaged for rotation with the second grip member 14 and engaged for sliding movement with the first grip member 12. As shown in detail in FIG. 4, the two arms 18, 20 are interlocked for rotation with respect to each other about a pivot member 22, such as a bolt. A resilient member 24 such as a coil spring is positioned to engage the arms 18, 20 and acts to bias the first arm 18 and second arm 20 of the scissor guide 16 in an outwardly expansive direction, thereby driving the first grip member 12 and second grip member 14 in opposed directions.

Referring to FIGS. 1 and 5, it can be seen that the grip members 12, 14 are composed of U-shaped channels 12A, 14A. The ends of the arms 18, 20 of the scissor guide 16 which are rotatably mounted in the channels 12A, 14A are each secured by means of pin 26. The opposed ends of the arms 18, 20 which are slidingly mounted in the channels 12A, 14A are each secured by means of a pin 26 engaging a slot 28.

A prosthesis retention member 30, composed of a seat member 31 and a cap member 40, is carried by the grip members 12, 14. Preferably, the seat member 31 is carried by the first grip member 12 and includes at least two retention cavities 32, 34 which are situated at different elevations with respect to each other as shown in FIG. 3. The first retention cavity 32 is designed to orient a patellar implant at a high elevation and retention cavity 34 is designed to orient a patellar implant at a lower elevation. Each retention cavity 32, 34 is conical in shape and includes a resilient means such as an O-ring 36 positioned to receive the curved or conical surface 38 of a patellar implant P as shown in FIG. 3. Thus, the patellar implant P is seated in the retention cavities 32, 34 by engagement with the O-ring and the conical surface 38 of the implant P is protected from any potential for marring or blemishing due to unwanted contact with hard edges or parts of the retention member 30.

The cap member 40 is carried by the second grip member 14 and includes a mating surface 42 designed to smoothly engage with the top surface 44 of the seat member 31. The cap member 40 also includes cavities 46, 48 designed to engage with the body portion 50 of the patellar prosthesis P when the cap member 40 is positioned in mating relationship with the seat member 31 as shown in FIG. 3. The cavities 46, 48 each include an indent 47, 49 for receiving an O-ring (not shown) if desired. The cavities 46, 48 each also include an aperture 51, 53 extending through the cap member 40 and aligned with the respective axial centerlines for each cavity 46, 48. The apertures 51, 53 are designed to receive the stem 52 of the implant P and allow the stem 52 to extend therethrough. When the cap member 40 is securely mated with the seat member 31, the patellar prosthesis P is securely fixed within the retention member 30, for instance between the retention cavity 32 and the cap cavity 46 while resting on the O-ring 36. The parallel orientation of the seat member 31 with the cap member 40 due to their being carried by the parallel oriented grip members 12, 14 will serve to properly orient the axis of the stem 52 of the implant P to be perpendicular to the cutting guide 54 of the cap member 40. Since the retention cavities 32 and 34 are on different elevational levels, the stem 52 will extend through the cap member 40, thereby exposing different lengths and providing for the stem 52 to be trimmed at the different lengths, depending on the needs of the surgeon after viewing the particular patella intended to receive the implant.

A locking member 55 consisting of a ball screw bolt 56 is fixed to the first grip member 12 and extends through the second grip member 14. A thumb nut 58 is engaged with the ball screw 56 and is utilized to move the cap member 40 into and out of engagement with the prosthesis retaining member 30. Examples of the range of movement are shown in FIGS. 1 and 3.

Referring now to FIGS. 6-9, an alternative embodiment of the patellar stem trimmer, generally designated by numeral 110 is shown. The stem trimmer 110 is preferably constructed of two distinct units: a generally Z-shaped member 114 forming an upper grip member 120 at one extreme and a pivot arm 117 at the opposed extreme; and a second handle member 114 generally shown to form a lower grip member 118 at one extreme and a generally U-shaped clamping member 119 at the opposed extreme. The Z-shaped member 112 and the second member 114 are pivotally interconnected at pivot point 121. A resilient means 124 is positioned between the upper grip member 118 and the lower grip member 120, acting to force the upper and lower grip members 118, 120 in an outwardly expansive resting position. It can be seen from viewing FIG. 6 that the farther the upper grip member 118 and the lower grip member 120 are separated, the farther the pivot arm 117 will be positioned away from the U-shaped member 119. A locking member consisting of a ball screw bolt 156 and a thumb nut 158 is engaged with the upper grip member 118 and lower grip member 120 to provide the specific desired limitations on the outward expansion of the grip members 118, 120 as caused by the resilient member 124.

The U-shaped member 119 of this embodiment preferably defines a cap member 140 on the uppermost oriented arm 123 of the U while the opposed arm 125 of the U extends parallel to the cap member 140. The end of the opposed arm 125 defines a guide 145 oriented with respect to the axial centerline of a cavity 146 located within the cap member 140. The cap member 140 is preferably removable from the arm 123 of the U-shaped member 119. As shown in FIGS. 6-9, the cap member 140 includes a stem portion 141 which is designed to mate with a female slot 143 located in the top arm 123 of the U-shaped member 119. A tightening nut 145 secures the cap member 140 in its desired engaged position within the slot 143. The cap member 140 includes a cavity 146 for engaging the body portion 150 of a patellar prosthesis P. As the body portion 150 of the patellar prosthesis is engaged by the cavity 146 of the cap member 140, the stem 152 of the body portion 150 extends through an aperture 151 located in the cap member 140 at the axial centerline of the cavity 146. A cutting guide 154 is located on the cap member 140 on the opposed side from the cavity 146. Thus, cap members of different cross-sectional thicknesses can be interchanged with the top arm 123 to provide for variable length stems 152 as shown in FIG. 7.

A centering member 127 is positioned on the centerline axis of the cap member 140 and includes a shaft member 129 extending through the guide 145. The shaft member 129 includes a prosthesis retention member 130 formed at the end closest in proximity to the cap member 140. The distal end of the shaft member 129 which is opposed to the prosthesis retention member 130 is engaged with the pivot arm 117. The prosthesis retention member 130 includes the same structure as the preferred embodiment described earlier with reference to FIG. 3, that is the retention member 130 includes a retention cavity 132 complete with O-ring 136 for receiving the conical surface 138 of the patellar prosthesis P.

Figure 7:
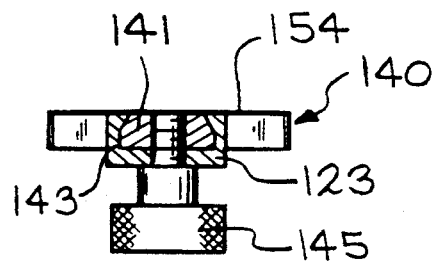
FIG. 7 is a sectional view taken along line 7—7 of FIG. 6.
Figure 8:
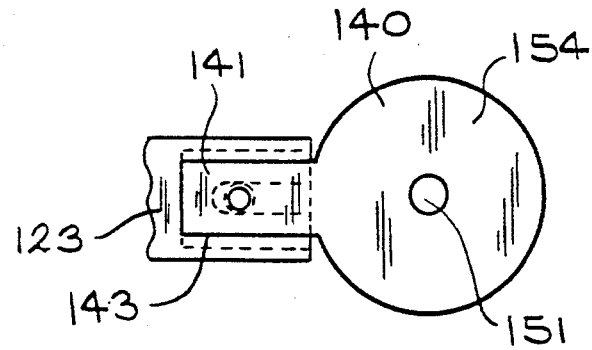
FIG. 8 is a fragmentary top plan view of the cap member of the stem trimmer of FIG. 6.
Figure 9:
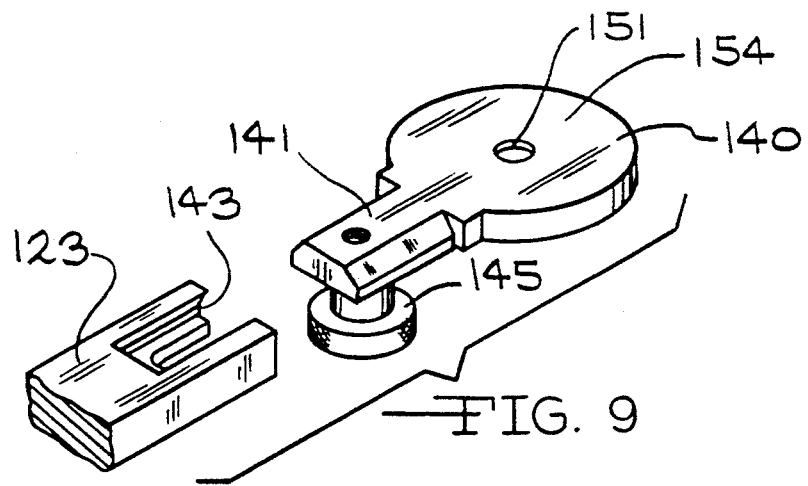
FIG. 9 is an exploded perspective view of the cap member of the stem trimmer of FIG. 6.

The engagement between the shaft member 129 and the pivot arm 117 is achieved by means of a sliding pivot joint shown in ghost in FIG. 6. The pivot joint consists of a ball member 131 formed on the end of the pivot arm 117. The ball member 131 is engaged in a retention slot 133 which allows the ball member 131 to slide in the retention slot 133 in a direction transverse to the movement of the shaft 129 along the centerline axis of the cap member 140.

Many modifications and embodiments will become readily apparent to those skilled in the art. Accordingly, the scope of the present invention should be determined only by the scope of the appending claims.

I claim:

1. A tool for use in adapting a patellar prosthesis, having a body portion and a stem portion extending from the body portion, to fit a specified human patella by trimming the stem of the patellar prosthesis comprising: a prosthesis retention member having a seat member and a separate cap member intended to engage with said seat member, said seat member including at least one cavity defining a centerline axis for receiving the prosthesis and orienting the prosthesis such that the stem extends away from said cavity along said centerline axis, said cap member including an aperture centered on said centerline axis for receiving the stem as said cap member is engaged with said seat member, a means for maintaining such centerline axis orientation between said cavity and said aperture as said cap member and said seat member are moved from a position of disengagement to a position of engagement, whereby the patellar prosthesis is securely retained within said retention member and a portion of the stem extends through said aperture and is exposed for trimming and removal.

2. The trimming tool of claim 1, wherein said cap member further includes a cutting guide disposed in perpendicular orientation to the axial centerline of the prosthesis stem.

3. The trimming tool of claim 1 further including a resilient means fixed about said cavity wherein the prosthesis is received by and rests upon said resilient means when the prosthesis is positioned in said cavity.

4. The trimming tool of claim 2, wherein said seat member includes a first retention cavity oriented at a specified elevation with respect to said cutting guide and a second retention cavity oriented at a second and different elevation with respect to said cutting guide and said cap member includes a first aperture aligned with said first cavity and a second aperture aligned with said second cavity, wherein the stem portion extending through said first aperture is exposed at a first length and the stem portion extending through said second aperture is exposed at a second and different length.

5. The trimming tool of claim 4 further including a first resilient means fixed about said first cavity wherein the prosthesis is received by and rests upon said first resilient means when the prosthesis is positioned in said first cavity and a second resilient means fixed about said second cavity wherein the prosthesis is received by and rests upon said second resilient means when the prosthesis is positioned in said second cavity.

6. The trimming tool of claim 1, wherein said seat member is integrally formed with a first grip member and said cap member is integrally formed with a second grip member and a guide means is interposed between said first and second grip members to maintain said grip members and, therefore, said cap member and said seat member in a fixed parallel relationship as said grip members are utilized to move said cap member and said seat member with respect to each other along such centerline axis.

7. The trimming tool of claim 6 further including a resilient member engaged with said first and second grip member for exerting a force upon said first and second grip members to move them expansively away from each other.

8. The trimming tool of claim 7 further including a locking member to hold said grip members in a desired orientation with each other and prevent such expansive movement as caused by said resilient member.

9. The trimming tool of claim 1 further including a first grip member fixed to said seat member and a second grip member engaging said cap member, said first and second grip members being affixed together such that movement of said second grip member towards and away from said first grip member creates concomitant movement of said seat member with respect to said cap member.

10. The trimming tool of claim 9, wherein said cap member is removable from its engagement with said second grip member and a variety of cap members of differing cross-sectional thicknesses are available for engagement with said second grip member, whereby different length portions of the stem extend through said aperture dependent upon the cross-sectional thickness of said cap member engaged with said second grip member.

11. The trimming tool of claim 9, wherein said seat member is supported by a shaft member.

12. The trimming tool of claim 11, wherein said centerline orienting means includes a centering member having a guide positioned about such centerline axis, said guide being adapted to engage said shaft and maintain said shaft in an oriented position on such centerline axis.

13. The trimming tool of claim 12, wherein said centering member is integrally fixed to said first grip member.

14. The trimming tool of claim 12, wherein said first grip member includes a pivot arm engaged with said shaft member, said pivot arm defining a ball member and said shaft member defining a retention slot for engaging said ball member wherein said ball member is free to move in a direction transverse to such centerline axis within said retention slot as said pivot arm moves said shaft member and said seat member along such centerline axis.

15. The trimming tool of claim 9 further including a resilient member engaged with said first and second grip members for forcing said grip members expansively away from each other.

16. The trimming tool of claim 15 further including a locking member to hold said grip members in a desired orientation with each other, and prevent such expansive movement as caused by said resilient member.

* * * * *